United States Patent [19]
Gutierrez et al.

[11] Patent Number: 5,466,875
[45] Date of Patent: Nov. 14, 1995

[54] PROCESS FOR THE PURIFICATION OF ALKALINE EARTH METAL SALTS OF 2,2'-OXYDISUCCINATE BY ACIDIFICATION

[75] Inventors: Eddie N. Gutierrez, Midland Park; Shang-Ren Wu, Mahwah, both of N.J.

[73] Assignee: Lever Brothers Company, Division of Conopco, Inc., New York, N.Y.

[21] Appl. No.: 323,320

[22] Filed: Oct. 14, 1994

[51] Int. Cl.⁶ .................................................. C07C 51/43
[52] U.S. Cl. ............................................ 562/580; 562/583
[58] Field of Search ...................................... 562/580, 583

[56] References Cited

U.S. PATENT DOCUMENTS

| | | | |
|---|---|---|---|
| 3,128,287 | 4/1964 | Berg | 260/346.8 |
| 3,635,830 | 1/1972 | Lamberti et al. | 252/152 |
| 3,914,297 | 10/1975 | Lamberti et al. | 260/535 P |
| 4,188,493 | 2/1980 | Walter | 562/580 |
| 4,798,907 | 1/1989 | MacBrair, Jr. et al. | 562/583 |
| 4,959,496 | 9/1990 | Crutchfield et al. | 562/583 |
| 5,030,751 | 7/1991 | Lamberti et al. | 562/583 |
| 5,068,420 | 11/1991 | Kreczmer | 562/583 |
| 5,068,421 | 11/1991 | Horng | 562/583 |
| 5,104,568 | 4/1992 | Shaw, Jr. et al. | 252/174.18 |
| 5,171,886 | 12/1992 | Schultz | 562/583 |
| 5,254,281 | 10/1993 | Pichardo et al. | 252/108 |
| 5,296,588 | 3/1994 | Au et al. | 536/1.11 |
| 5,336,765 | 8/1994 | Au et al. | 536/18.5 |

FOREIGN PATENT DOCUMENTS 2030985   6/1991   Canada.

OTHER PUBLICATIONS

Abstract of JP 4112849. (1992).
Abstract of JP 4112850. (1992).
Defense Publication No. T. 101,805—published May 4, 1982.

*Primary Examiner*—José G. Dees
*Assistant Examiner*—Barbara S. Frazier
*Attorney, Agent, or Firm*—James J. Farrell

[57] ABSTRACT

A process for the purification and recovery of 2,2'-oxydisuccinate moieities from a reaction mixture containing maleate, malate, fumarate, and alkaline earth metal is disclosed which reduces the pH to about 3.8 to 4.2 with sulfuric acid and then produces the calcium salt of the 2,2'-oxydisuccinate by heating and precipitation.

11 Claims, No Drawings

PROCESS FOR THE PURIFICATION OF ALKALINE EARTH METAL SALTS OF 2,2'-OXYDISUCCINATE BY ACIDIFICATION

BACKGROUND OF THE INVENTION

1. Field of the Invention

The invention relates to the purification and recovery from a reaction mixture of the alkaline earth metal salt of 2,2'-oxydisuccinic acid by a process which produces the salt in very high purity while substantially avoiding contamination of the reaction mixture with undesirable reaction products and solvents. 2,2'-oxydisuccinic acid and salts thereof are effective sequestering agents and are useful as builders in detergent compositions for household, institutional and industrial use.

2. Related Art 2,2'-oxydisuccinic acid (ODS) and salts thereof are known to have utility as sequestering agents and detergent builders. A disadvantage of ODS and its salts as detergent builders is that they may be relatively expensive to prepare.

U.S. Pat. No. 3,128,287 to Berg discloses a preparation of ODS salt by admixing maleic acid with an excess of calcium, barium, magnesium or strontium hydroxide in the presence of water, then heating the reaction mixture from about one day to about one month at temperatures ranging from 50° C. to reflux temperatures. The process yields a mixture of malic acid and ODS. Berg's Example I teaches a preparation of ODS, where an aqueous mixture of maleic anhydride and calcium hydroxide is reacted at reflux (100° C.) for 4 days. Subsequently, ODS salt is isolated from the product containing ODS and malic acid salts by various methods.

U.S. Pat. No. 3,635,830 to Lamberti et al., discloses a process for the preparation of ODS based on the process of Berg. The patent teaches separation/purification of two diastereoisomeric forms of ODS obtained by the Berg process. The patent also discloses detergent compositions comprising ODS or salts thereof as detergent builders.

U.S. Pat. No. 5,030,751 to Lamberti discloses methods of making mixed ODS/CMOS salts and separation by solvents.

U.S. Pat. No. 5,068,420 to Kreczmer discloses alkaline alcohol extraction to purify ether carboxylate salts.

U.S. Pat. No. 4,959,496 to Crutchfield discloses processes for the preparation of ether carboxylate where unreacted starting acids are recovered.

U.S. Pat. No. 3,914,297 to Lamberti employs ion exchange resins and acetone to recover various ether polycarboxylate salts.

A workable and cost-efficient production of ODS salt must be directed towards optimizing the process conditions in such a manner that the salts can be easily obtained in high yield without having to resort to expensive solvents which also must be disposed of after use. There have been different approaches to the problem of producing ODS in high yield at a low cost. However, none of these approaches has been completely satisfactory.

Accordingly, it is an object of the present invention to provide a process which produces the alkaline earth metal salt of ODS in high purity and high yield.

This and other objects and advantages will appear as the description proceeds.

SUMMARY OF THE INVENTION

The attainment of the above objects is made possible by this invention which includes a purification of the alkaline earth metal salt of ODS from a reaction mixture by a process comprising the steps of:

(i) preparing an aqueous reaction mixture containing primarily alkaline earth metal, preferably calcium, ODS in solution;

(ii) reducing the pH of the solution to about 3.8 to 4.2 with sulfuric acid or hydrochloric acid or ion exchange resin;

separating the alkaline earth metal sulfate formed, if any;

(iv) heating the separated solution at a temperature of about 90° C. to 100° C. for about 2 to 8 hours to form a precipitate of alkaline earth metal ODS salt; and (v) recovering the ODS salt.

The alkaline earth metal ODS in the aqueous reaction mixture can be prepared by any method known in the art. For example, by the method disclosed in copending patent application Ser. No. 08/198,401 and incorporated herein by reference.

In its broadest aspect, the invention provides a process for recovering an alkaline earth metal salt, preferably a calcium salt, of ODS which may be isolated from other organic species contained in the reaction product and converted to ODS acid (Formula I below)

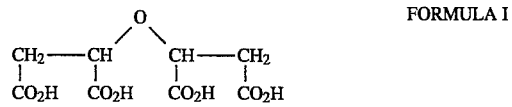

FORMULA I or other ODS salts such as monovalent cation salts, ammonium salts, morpholinium salts, alkanol ammonium salts and mixtures thereof, by methods known in the art. Such methods are disclosed, for example, in U.S. Pat. No. 3,128,287 to Berg and U.S. Pat. No. 3,635,830 to Lamberti et al. discussed above and incorporated herein by reference. As noted, the U.S. Pat. No. 3,635,830 patent also discloses detergent compositions containing ODS or salts thereof.

In defining the ODS salt purification and recovery process of this invention it is intended to include both batch and continuous processes.

DETAILED DESCRIPTION OF THE INVENTION

The inventive process of this invention for obtaining purified alkaline earth metal salts of ODS in high yield while minimizing byproducts is outlined as follows:

(i) preparing an aqueous reaction mixture containing alkaline earth metal ODS salts, preferably calcium ODS salts. The mixture is acidified with sulfuric acid or hydrochloric acid to a pH of about 4.0. Free calcium ions will react and precipitate as calcium sulfate if the sulfuric acid is used if hydrochloric acid is used there will be no substantial precipitate. The precipitated calcium sulfate, if any, is filtered off and the supernatant is heated at a temperature of about 9° C. to 100° C. for 2 to 8 hours and then allowed to cool. Calcium ODS will precipitate out in good yield and purity and can then be recovered and converted to the appropriate salts such as, for example, the sodium salt.

The process of this invention for the purification of the alkaline earth metal salt of ODS includes preparing an aqueous mixture of alkaline earth metal ODS preferably calcium.

The alkaline earth metal in the reaction mixtures of the inventive process may be selected from the group consisting of barium, strontium or calcium. The most preferred alkaline earth metal for use in this invention is calcium.

The ODS salt forming reaction is conducted at high concentration in aqueous media to afford efficacy and high throughput. The amount of water present may vary and is preferably sufficient to permit the reaction to proceed with the amount of water being about 40% to 95%. The amount may, however, be more or less depending on design parameters.

Desirably, the reactants of the starting mixture for the process are combined in water using physical agitation. In the preferred embodiments of the invention, an alkaline earth metal hydroxide is mixed with an aqueous mixture of the malate and maleate moieties producing what is believed to be a soluble mixed calcium complex, solid malate and maleate may also be used.

The reaction temperature for the purification is about 90° C. to 100° C., for at least about 2 hours and preferably no longer than about 8 hours. The aqueous reaction product mixture typically contains a mixture of alkaline earth metal salts of 2,2'-oxydisuccinate, malate, maleate and fumarate. The reaction products obtained contain the alkaline earth metal salt of ODS, preferably calcium.

The pH is reduced to 4 by appropriate acidifying means such as sulfuric acid, ion exchange resins or hydrochloric acid. If sulfuric acid is used, the resulting calcium sulfate precipitate can be removed from the aqueous reaction product mixture by filtration. If ion exchange resins are used, the ion exchange resins may be filtered out. If hydrochloric acid is used, soluble chloride salts are formed. The calcium ODS left in solution is then heated at 90° C. to 100° C. for 2 to 8 hours whereby a precipitate forms. The solution is allowed to cool and a precipitate is then collected in a high degree of purity. The other salts, e.g., fumarate, maleate and malate are left in the supernatant liquid after recovery.

Ultimately for use, the calcium content of the ODS salt prepared by the inventive methods herein should desirably be reduced to the extent that calcium is present in an amount of no more than about 1.0% of the ODS salt and preferably less than 0.2%, in order to form compositions particularly suitable as detergent builders. This can be accomplished by the method of defensive publication T 101,805.

ODS salts formed herein are of extremely high purity but if necessary, they can also be treated, after calcium removal, in a further step, using organic or aqueous solvent extraction to remove excess reactants, such as maleates, or organic reaction by-products, such as fumarates. This can, for example, be accomplished by conventional salt separation procedures using a solvent such as a mixture of methanol and water (4:1 v/v) in which these excess reactants and reaction by-products are relatively soluble and in which the desired ODS salt is relatively insoluble as disclosed in U.S. Pat. No. 5,068,420.

At any stage after the ODS salt formation, and after reducing the calcium salt content the reaction product can be concentrated by removal of water to the desired extent. Water removal can, for example, after calcium removal, involve substantially complete drying of the reaction product mixture, e.g., by spray drying, so that the ODS salt is recovered in solid, e.g., granular, form. The sodium salt of ODS in the form of aqueous liquid may be utilized directly in the preparation of detergent compositions or laundry additive products of the types more fully described hereinafter.

It is also possible, if desired, to acidify the product mixtures using conventional acidification or ion exchange techniques to convert the ODS salts to their free acid form. Normally, however, the ODS materials of this invention can, after calcium depletion or complete replacement by sodium, be used as builders in their water-soluble salt form, and such acidification is therefore not usually necessary or desirable.

When converted into suitable form, the ODS salts can be used as sequestering builders in a wide variety of detergent or laundry additive compositions.

Detergent compositions incorporating the ODS salt prepared using the processes of this invention contain as essential components from about 0.5% to about 98% of a surfactant and from about 2% to about 99.5% of the ODS compounds as a detergency builder, generally in sodium-salt form. Surfactants that are useful in the present invention are the anionic (soap and nonsoap), nonionic zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and Berch, the disclosures of which are incorporated by reference herein. The ODS builder can be used either as the sole builder or where desired, can be used in conjunction with other well-known builders, examples of which include water-soluble salts of phosphates, pyrophosphates, orthophosphates, polyphosphates, phosphonates, carbonates, polyhydroxysulfonates, polyacetates, carboxylates, polycarboxylates, succinates and the like.

In addition to the surfactant and builder, there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from about 9 to about 11.

In addition to their utility as builders in detergent and laundry additive compositions, the ODS salts of the invention can, after reducing their calcium content, also be utilized in other contexts wherein water hardness sequestration is required. Other uses are provided in water softening compositions, devices and methods and boiler descaling compositions and methods. It is also theorized that ODS can complex heavy metals which react with bleach and thus can stabilize bleach.

It should also be noted that when ODS is employed as the free acid or as partly neutralized salt, it has utility in metal cleaning composition under pH conditions of about 2 to about 5. The following examples are designed to illustrate, but not to limit, the practice of the instant invention. All percentages and parts herein are by weight unless indicated otherwise. All ratios herein are mole ratios unless indicated otherwise. R, S-malic acid is used in the Examples unless indicated otherwise.

Reaction mixture samples and reaction products were analyzed by HPLC and/or NMR. The HPLC analysis is carried out using a Hitachi instrument. The mobile phase is a 30/70 acetonitrile/water mixture with 0.75 g/l of 85% phosphoric acid at a pH of about 3 to 4. The column is an RP/SAX Regis 25 cm ×4.6 mm in dimension. The flow rate is 1.5 ml/minute. The wavelength at which the detector is set is 210 nm. Samples are diluted with the mobile phase. Quantification is done using an external standard. The volume of the injections used are 50 μl.

The NMR is a 200 MHz Bruker model. Samples are prepared by ion exchanging the calcium salts, followed by neutralization of the acids with sodium carbonate, drying and dissolution in $D_2O$. Peak assignments are as follows:

Fumaric 6.28δ

Maleic 5.78δ

Malic CH 4.1 to 4.3δCH$_2$ 2.0 to 2.5δ (overlap with ODS)

ODS CH 3.83 to 3.59δCH$_2$ 2.0 to 2.5δ (overlap with malic)

EXAMPLES

EXAMPLE 1

A dry mixture of 106.8 g (0.92 mole) maleic acid and 100 g (0.75 mole) malic acid is added to 136 g (1.8 mole) of $Ca(OH_2)$ in 464 ml water, while the temperature is maintained at 55° C. The hazy mixture is then stirred for 6 hours at 65°–70° C. and 16 hours overnight at room temperature.

|  | WEIGHT % | | | |
| --- | --- | --- | --- | --- |
|  | ODS | MALIC | MALEIC | FUMARIC |
| NMR | 79.0 | 10.9 | 9.2 | 0.9 |

Precipitation Under Refluxing Conditions

Four aliquots of 311.7 g of Solution I are placed into four separate beakers. Into beaker 1 is added 32.8 g (0.33 mole) of sulfuric acid to pH 1. Into beaker 2 is added 21.8 g (0.22 mole) of sulfuric acid to pH 2. Into beaker 3 is added 11 g (0.11 mole) of sulfuric acid to pH 4. Into beaker 4 is added 5.5 g (0.055 mole) sulfuric acid to pH 5. All the solutions are stirred for 1.5 hours and the calcium sulfate that precipitates is filtered. Filtrate 1 is refluxed for 15 hours, filtrates 2 and 3 are refluxed for 8 hours and filtrate 4 is refluxed for 2 hours.

Filtrate 1 produces no calcium ODS, filtrates 2 and 3 produce 19 g and 48 g of calcium ODS, respectively, (after drying at 125° C. overnight) and filtrate 4 produces a gelled unstirrable mixtures. Analysis of calcium ODS from filtrates 2 and 3 is as follows:

| (by the HPLC method mentioned above) WEIGHT % | | | | |
| --- | --- | --- | --- | --- |
| Solid | ODS | Malic | Maleic | Fumaric |
| 2 | 98.9 | 0.3 | 0.3 | 0.4 |
| 3 | 99.8 | — | 0.18 | (maleic and fumaric) |

EXAMPLE 2

To 311.7 g of a solution prepared as above but containing 75.2% ODS, 12.5% malic, 11.7% maleic and 0.7% fumaric, is added 11 g (0.11 mole) of sulfuric acid to pH 4 and the mixture stirred for 1.5 hours. The calcium sulfate that forms is filtered and the solution is stirred at 90° C. for seven hours. The solid which precipitates is filtered and dried at 125° C. overnight to afford 50 g of Ca ODS.

| WEIGHT % | | | |
| --- | --- | --- | --- |
| ODS | Malic | Maleic | Fumaric |
| 97.2 | 1.9 | 0.8 | — |

EXAMPLE 3

Comparative Example Prepared Using a Mixture of Calcium and Sodium Hydroxide

To a slurry of 10.2 g (0.255 mol) sodium hydroxide, 7.1 g (0.093 mol) calcium hydroxide and 28 g water is added gradually a dry mixture of 10 g (0.11 mol) maleic anhydride and 12.7 g (0.93 mol) dl malic acid pH 12.9. The hazy solution is heated to 65° C. four hours, stirred overnight at 25° C. and an additional three to four hours at 40° C. $^1$H NMR analysis shows the following weight % of products:

| WEIGHT % | | |
| --- | --- | --- |
| ODS | MALIC | MALEIC |
| 65.4 | 17.3 | 17.1 |

To this mixture is added 12.5 g of concentrated hydrochloric acid to lower the pH to 4.05. The solution is heated to reflux for three to four hours and the solid that precipitates out, 12.6 g is a mixture of calcium ODS and some calcium maleate. This is recovered. Because of the presence of maleic impurities in the solid, the solid precipitate was redispersed in 100 ml water (overnight) and filtered. The water soluble components are essentially maleate with traces of ODS. The insoluble component, 10.1 g is calcium ODS and consists of the following measured as sodium salts:

| WEIGHT % | | |
| --- | --- | --- |
| ODS | MALIC | MALEIC |
| 99.1 | 0.7 | 0.2 |

The solution obtained above after removal of calcium ODS precipitate is allowed to stand and precipitates out 1.2 g of mono sodium maleate. Workup affords (by $^1$H NMR) the following ratio of products measured as sodium salts:

| WEIGHT RATIO INCLUDING WATER | | | |
| --- | --- | --- | --- |
| ODS | MALIC | MALEIC | FUMARIC |
| 75.9 | 15.8 | 3.4 | 4.9 |

It is understood that the examples and embodiments described herein are for illustrative purposes only and that various modification or changes in the light thereof will be suggested to persons skilled in the art and are to be included within the spirit and purview of this application and the scope of the appended claims.

What is claimed is:

1. A process for preparing the alkaline earth metal salt of 2,2'-oxydisuccinic acid in high purity comprising:
  (i) preparing an aqueous solution of said alkaline earth metal salt in a reaction mixture;
  (ii) adding sufficient acidifying agent to said reaction mixture to achieve a pH of about 3.8 to 4.2 to form an acidified reaction mixture;
  (iii) heating said acidified reaction mixture to a temperature of 90° C. to 100° C. for at least 2 hours to form the alkaline earth metal salt of ODS;
  (iv) precipitating the alkaline earth metal salt of ODS;
  (v) recovering the alkaline earth metal salt of ODS as a product.

2. A process as defined in claim 1 wherein the reaction is extended for a period of about 8 hours at a temperature of less than about 100° C.

3. A process as defined in claim 1 wherein the alkaline earth metal is calcium.

4. A process as defined in claim 1 wherein the pH is 4.0.

5. A process as defined in claim 1 wherein the acidifying agent is selected from the group consisting of sulfuric acid, hydrochloric acid and ion exchange resin.

6. A process as defined in claim 1 wherein the acidified solution is filtered to remove any precipitate before heating.

7. A method for purifying the product obtained from claim 1 by contacting the reaction mixture from step ii with a mixed methanol/water solvent after reducing the calcium content of the product.

8. A process as defined in claim 1 wherein the concentration of maleic and malic species as the calcium salt at the beginning of the reaction is about 5 to 60%.

9. A process as defined in claim 1 wherein the concentration of maleic and malic species as the calcium salt at the beginning of the reaction is about 40% to 50%.

10. A process as defined in claim 1 wherein the alkali metal content is less than about 0.001 mole.

11. A process as defined in claim 1 having less than about 0.001 mole of sodium.

* * * * *